United States Patent

Beer et al.

[11] Patent Number: 5,292,007
[45] Date of Patent: Mar. 8, 1994

[54] METHOD OF AND APPARATUS FOR CONTINUOUS NON-DESTRUCTIVE TESTING OF BAR-SHAPED SPECIMENS

[75] Inventors: Gerhard Beer, Paderborn; Georg Kellersohn, Bad Driburg, both of Fed. Rep. of Germany

[73] Assignee: Benteler Aktiengesellschaft, Paderborn, Fed. Rep. of Germany

[21] Appl. No.: 667,426

[22] Filed: Mar. 11, 1991

[30] Foreign Application Priority Data

Mar. 15, 1990 [DE] Fed. Rep. of Germany ....... 4008300

[51] Int. Cl.$^5$ ............................................. B07C 5/14
[52] U.S. Cl. ................................. 209/518; 209/556; 209/571; 209/605; 324/227; 324/238
[58] Field of Search ............... 209/517, 518, 552, 556, 209/567, 571, 587, 590, 605; 324/237, 238, 240, 227

[56] References Cited

U.S. PATENT DOCUMENTS

| | | | |
|---|---|---|---|
| 2,781,905 | 2/1957 | Phillips | 209/518 |
| 2,885,076 | 5/1959 | House et al. | 209/556 |
| 3,010,577 | 11/1961 | Anderson et al. | 209/556 |
| 4,335,352 | 6/1982 | Stephen | 209/567 X |
| 4,576,286 | 3/1986 | Buckley et al. | 209/590 X |
| 4,787,549 | 11/1988 | Matay et al. | 209/518 X |

Primary Examiner—H. Grant Skaggs
Assistant Examiner—Tuan N. Nguyen
Attorney, Agent, or Firm—Anderson Kill Olick & Oshinsky

[57] ABSTRACT

Method of and apparatus for continuous non-destructive testing of bar-shaped specimens formed of iron-containing material of specific quality characteristics, where the bar-shaped specimens, such as pipes, move on a roll table (2) along an elongated path through two testing blocks (8, 9) spaced apart along the path. The testing blocks (8, 9) are mechanically decoupled from one another and are logically linked to an electronic testing installation (10). As a specimen moves through a first testing block (8) a signal is developed indicating the presence or absence of flaws and their location in the specimen. The location is referred to the length of the specimens. The testing blocks (8, 9) are located between a supply station (1) and a sorting station (3) with the roll table (2) extending between the two stations. Based on the signals generated, the specimens are sorted in the sorting station between an accepted tray (4) and a number of rejected trays (5, 6, 7) for reworkable or scrap specimens.

5 Claims, 1 Drawing Sheet

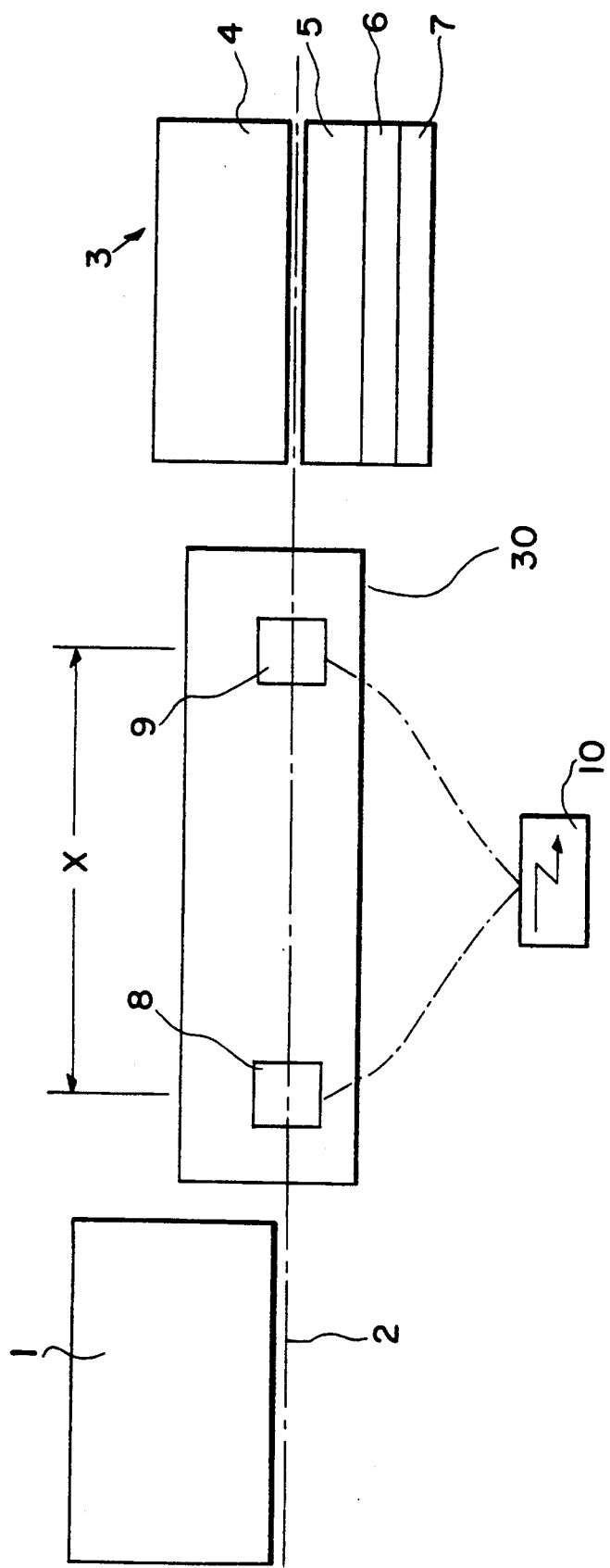

METHOD OF AND APPARATUS FOR CONTINUOUS NON-DESTRUCTIVE TESTING OF BAR-SHAPED SPECIMENS

BACKGROUND OF THE INVENTION

The present invention is directed to a method of and apparatus for continuous non-destructive testing of bar-shaped specimens formed having iron-containing material of specific quality characteristics. Individual specimens are moved at a definite translational velocity along an elongated path through a testing block which is coupled to an electronic testing installation for continuously comparing the specimens passing through the testing block via the electronic testing installation with calibrated artificial flaws of a defined magnitude previously stored in the testing installation. The specimens are classified based on the comparison afforded by the testing installation.

Bar-shaped specimens, particularly in the form of pipes or tubular members, are examined, during the course of a continuous passage, in accordance with preset standards in order to determine the presence or absence of flaws for assuring the quality characteristics described in an applicable specification. Mainly the testing processes used are based on magnetic induction or on acoustics. In both cases, a testing block is coupled to an electronic testing installation which has been calibrated with the help of a testing standard containing artificial flaws of a defined magnitude. When the testing standard is introduced into the testing block, the artificial flaws generate characteristic signals due to a change in the magnetic field (magnetic induction process) or by reflection (acoustic process). The amplitude level of the signals is arranged by suitable actuation links in the testing installation so that two response ranges are formed and assigned respectively to specific sorting compartments or trays in a sorting station. In the sorting station one sorting compartment receives accepted specimens while the other sorting compartment receives rejected specimens, that is specimens with a certain level of flaws.

The specimens, such as pipes, are located in a supply station which also serves as a material buffer, and are consecutively displaced from the supply station onto a roll table and conveyed therealong at a specific translational velocity through the testing block. Any specimen generating signals of an amplitude level in the testing block—electronic testing installation, equal to or larger than the amplitude level of the testing standard, are stored in the sorting compartment for defective specimens after they have passed through the testing block. Specimens causing no amplitude or amplitude levels lower than that of the testing standard, are stored in the sorting compartment for flaw-free specimens.

In actual practice, it has been found that the defective specimens contain a relatively high proportion of specimens which have signaled false or pseudo flaws during testing. As a result, the defective specimens are subjected to a repeat examination under the same testing conditions, for eliminating as many as possible pseudo flaws signaled during the initial testing operation. Pseudo flaws can occur due to external interference effects, such as controlled pulses, inductions triggered by control processes, uneven and/or erratic translation movement, off-centered guidance or by blows or shocks applied to the specimens. Such interference effects generate pulses in the electronic testing installation which are evaluated as flaw signals with the result that such specimens are identified as containing flaws.

The disadvantage in the known process and apparatus is that the repeat testing occurs at a time interval from the initial testing. Apart from the fact that each rejected specimen must be especially designated as such and subjected to further quality testing, with the requirement for appropriate conveying means and conveying tracks with buffer zones, the repeat testing has negative effects especially in interconnected manufacturing facilities located upstream and downstream of the testing devices, if the testing device is integrated into a cyclically flowing production line. In addition, in the known situation no precise interrelationship between the signals displayed by the electronic testing installation and the various flaw conditions in the specimens can be acquired. A subsequent machining for specific types of flaws in the specimen is essentially out of the question.

SUMMARY OF THE INVENTION

Therefore, the primary object of the present invention is to improve the known method and apparatus as set forth above, so that by providing at least an indirect signal-flaw correlation, separate repeated testing can be avoided and the economic output per unit of time can be increased.

In accordance with the present invention, a second testing block is positioned in the path of the specimens on the roll table downstream of the first testing block for checking the presence of flaws determined by the first testing block. The spacing of the mechanically decoupled testing blocks arranged one following the other has an effect on the length of the testing path or on the arrangement of the entire testing line and on the testing and evaluation electronics that are used. The spacing between the two testing blocks can be changed.

If a specimen, such as a pipe, is passed along the testing path and if no flaw signal is generated by the specimen in the first testing block, then it passes through the second testing block without activating such block. After leaving the second testing block, the specimen arrives in the sorting station and due to the appropriate coupling of the electronic testing installation and the sorting station, it is deposited in the accepted tray or compartment.

If the specimen produces a flaw signal in the first testing block, which signal is differentiated within the electronic testing installation according to the type of the signal and location of the signal, then the second testing block is activated. Next the specimen passes through the second testing block and the signal type as well as signal location with reference to the length of the specimen must be confirmed for corroborating the flaw signal in the electronic testing installation.

If the signal type and signal location obtained from the first testing block are not confirmed, then the flaw signal in the electronic testing installation is erased and the specimen is directed to the accepted tray or compartment in the sorting station. In such a situation, in accordance with the invention, it is assumed that either external interference effects existed during the testing in the first testing block or that a pseudo flaw was signaled.

If, however, different signals appear in both testing blocks, then the flaw signal is evaluated with respect to the higher reproducability and the specimen is directed either to the rejected tray corresponding to the above-mentioned reproducability with regard to which reworkability of the specimen is concerned, or it is directed to the rejected tray for receiving scrap which cannot be reworked.

Initially, a noticeable advantage of the invention is that a considerable increase of the testing capacity is achieved, since the specimens are subjected to multiple testing in their passage along a single testing path. This particular economic advantage is especially noticeable in interconnected production lines in which the inventive testing device can be integrated. The capacity increase corresponds to the quantity which would have been subjected to a separate testing if the invention was not used.

Another advantage of the invention is the capability of differentiating between genuine (reproducible) and not genuine (not reproducible) flaw signals by the specific logic linkage of the two testing blocks with the electronic testing installation. The testing logic can also compensate to a large extent for external disturbances and a considerable reduction of false rejections can be achieved. Moreover, a perfect selection of borderline flaws can be achieved by establishing a multiple threshold in the testing blocks or in the electronic testing installation. Finally, an improved condition of the quality of the specimens as well as the quality of the testing procedure can be achieved by an installed redundance.

The various features of novelty which characterize the invention are pointed out with particularity in the claims annexed to and forming a part of this disclosure. For a better understanding of the invention, its operating advantages and specific objects attained by its use, reference should be made to the accompanying drawings and descriptive matter in which there are illustrated and described preferred embodiments of the invention.

BRIEF DESCRIPTION OF THE DRAWINGS

FIG. 1 is a schematic view of the invention.

DETAILED DESCRIPTION OF THE INVENTION

In FIG. 1 a supply station 1 contains a number of specimens in the form of pipes. The supply station 1 acts as a material buffer if it is connected to a manufacturing installation.

A roll table 2 with a regulatable velocity, extends from the supply station 1 to a sorting station 3 and forms a testing path for the specimens. Sorting station 3 includes an accepted specimen tray or compartment 4, a rejected specimen tray 5 for a flaw type A of the specimen which can be reworked, a rejected specimen tray 6 for a flaw type B of a specimen which can also be reworked, and a rejected specimen tray 7 for specimens which cannot be reworked and thus constitute rejects or scrap. Between the supply station 1 and the sorting station 3 along the testing path there are two testing blocks 8, 9 separated in the testing path direction by a spacing X. The spacing between the testing blocks 8, 9 can be changed and they are decoupled from one another mechanically but are logically interconnected through an electronic testing installation 10 for evaluating the signal type as well as the signal location with reference to the length of a specimen. Block diagram 30 is a schematic illustration of the adjusting means for adjusting the spacing between the first and second testing blocks (8, 9).

When a specimen is removed from the supply station 1 and moves individually along the roll table 2, initially it is transported by the table through the first testing block 8. If the specimen does not generate a flaw signal in the first testing block 8, then the downstream or second testing block 9 remains inactive and, upon reaching the sorting station, the specimen is directed into the accepted tray 4. The sorting operation is effected by an appropriate interconnection of the sorting station 3 with the electronic testing installation 10.

If a specimen passing through the first testing block 8 generates a flaw signal, which is differentiated or analyzed in the testing installation 10 as to signal type and signal location, the downstream second testing block 9 is activated. As the specimen passes through the second testing block 9, this block must confirm the signal type and also the signal location with reference to the length of the specimen.

If the signal type and signal location, determined by the first testing block, is not confirmed by the second testing block, then the flaw signal contained in the electronic testing installation 10 is erased and the specimen is directed into the accepted tray 4 of the sorting station 3. In such a situation it is assumed that the signal developed in the first testing block 8 resulted from an external disturbance or that a border line type of flaw was noted.

If different types of signals are obtained from the two testing blocks 8, 9, then the specimen is evaluated according to the flaw signal with the higher reproducability and it is placed in the appropriate rejected tray 5, 6 to be reworked, or in the rejected tray 7 for scrap.

The calibration of the electronic testing installation 10 takes place during the setup operation of the installation by introducing a standard test specimen containing artificial flaws of defined magnitude and passing the standard test specimen through the testing blocks 8, 9. Accordingly, the artificial flaws generate characteristic signals through changes in the magnetic field in a magnetic induction method or through reflection in a acoustic method. The amplitude level of such signal can be changed by actuation links in the installation. As a rule, the amplitude level is selected by changing the sensitivity of the apparatus whereby stepped response thresholds are established for sorting the specimens directed to the downstream storage station into the accepted tray or compartment 4 or to the rejected compartments of trays 5, 6 and 7.

While specific embodiments of the invention have been shown and described in detail to illustrate the application of the inventive principles, it will be understood that the invention may be embodied otherwise without departing from such principles.

We claim:

1. Method of continuous non-destructive testing of bar-shaped specimens formed of iron containing materials of specific quality characteristics, comprising the steps of moving individual specimens at a definite translational velocity along an elongated path through a first testing block (8) coupled to an electronic testing installation (10), continuously comparing the specimens passing through the first testing block (8) via the electronic testing installation (10) with calibrated artificial flaws of a defined magnitude previously stored in the testing installation, and after passing the first testing block (8) classifying the specimens based on the comparison afforded by the testing installation, wherein the improvement comprises the steps of providing at least a second testing block (9) in the elongated path spaced downstream from the first testing block (8) with the second testing block coupled to the electronic testing installation (10) and with the first and second testing blocks logically linked together through the electronic testing installation, continuously comparing the specimens passing through the second testing block (9) via the electronic testing installation (10) with the calibrated artificial flaws of defined magnitude stored in the testing installation, and sorting the specimens into accepted and rejected specimens based on the amplitude level of signals from the electronic testing installation in a sorting station connected to the testing installation and downstream of the testing blocks (8, 9).

2. Method, as set forth in claim 1, dividing the specimens in the sorting station, based on signals from the electronic testing installation, into accepted specimens, rejected specimens to be reworked and rejected specimens to be scrapped.

3. Method of continuous non-destructive testing of bar-shaped specimens formed of two iron containing materials of specific quality characteristics, comprising the steps of moving individual specimens at a definite translational velocity along an elongated path through a first testing block (8) coupled to an electronic testing installation (10), continuously comparing the specimens passing through the first testing block (8) via the electronic testing installation (10) with calibrated artificial flaws of a defined magnitude previously stored in the testing installation, and after passing the first testing block (8) classifying the specimens based on the comparison afforded by the testing installation, wherein the improvement comprises the steps of providing at least a second testing block (9) in the elongated path spaced downstream from the first testing block (8) with the second testing block coupled to the electronic testing installation (10) and with the first and second testing blocks logically linked together through the electronic testing installation, continuously comparing the specimens passing through the second testing block (9) via the electronic testing installation (10) with the calibrated artificial flaws of defined magnitude stored in the testing installation, and sorting the specimens into accepted and rejected specimens based on the amplitude level of signals from the electronic testing installation in a sorting station connected to the testing installation and downstream of the testing blocks (8, 9) wherein if the first testing block—electronic testing installation notes a specimen is flaw free, maintaining the second testing block inactive and passing the flaw free specimen to an accepted tray in the sorting station.

4. Apparatus for continuous non-destructive testing of bar-shaped specimens formed of iron-containing materials of specific quality characteristics, comprising a supply station (1) for specimens, a sorting station (3) spaced from and connected with the supply station by a roll table (2) having a regulated velocity, said roll table (2) forming an elongated path between said supply station and sorting station, a first testing block (8) located in the elongated path, an electronic testing installation (10) coupled to said first testing block and calibrated with respect to artificial flaws of defined magnitude in the specimens, wherein the improvement comprises at least one second testing block (9) located in the elongated path spaced downstream from said first testing block (8) and upstream from said sorting station and coupled to said electronic testing installation (10) with said first and second testing blocks (8, 9) logically linked together through the electronic testing installation, said testing installation (10) arranged to evaluate signals from said first and second testing blocks and signal locations referred to the specimen length, and said sorting station (3) in operative communication with said electronic testing installation (10) and having a level of flaw below a given level and a number of reject trays corresponding to various levels of flaws above the given level, said sorting being based on the amplitude level of signals from the electronic testing installation.

5. Apparatus, as set forth in claim 4, wherein said first and second testing blocks (8, 9) have adjusting means for adjusting the spacing between each other along the elongated path.

* * * * *